United States Patent [19]

Samour et al.

[11] 4,101,668
[45] Jul. 18, 1978

[54] ANTIOSTEOPOROTIC AGENTS

[75] Inventors: Carlos M. Samour, Wellesley, Mass.; Julius A. Vida, Greenwich, Conn.

[73] Assignee: Bristol-Myers Company, New York, N.Y.

[21] Appl. No.: 795,570

[22] Filed: May 10, 1977

[51] Int. Cl.² .............................................. A61K 31/38
[52] U.S. Cl. .................................................... 424/275
[58] Field of Search ........................................ 424/275

[56] References Cited

U.S. PATENT DOCUMENTS

| | | | |
|---|---|---|---|
| 3,655,697 | 4/1972 | Shen et al. | 424/275 |
| 3,674,875 | 7/1972 | Shen et al. | 424/275 |
| 3,784,602 | 1/1974 | Frei et al. | 424/275 |
| 3,803,180 | 4/1974 | Berger et al. | 424/275 |
| 3,953,601 | 4/1976 | Bondesson et al. | 424/275 |
| 3,975,403 | 8/1976 | Gante et al. | 424/275 |

Primary Examiner—Stanley J. Friedman
Attorney, Agent, or Firm—Morton S. Simon; Robert H. Berdo

[57] ABSTRACT

It is disclosed that compounds of the formula:

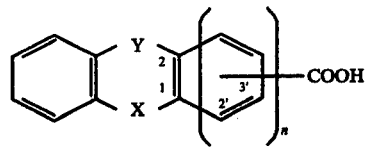

wherein Y represents $(C=O)_m$ in which $m$ has a value of 0 or 1; $n$ has a value of 0 or 1; and X represents S, NH or O; provided that there is a COOH substituent at the 1, 2 or 3 position relative to the X group; and further provided that when X is NH and $n$ is 0, the COOH group cannot be at the 2 position; and further provided that when $n$ is 0, the carboxyl group is attached to the ring containing the X and Y ring members or a non-toxic, pharmaceutically acceptable salt thereof are capable of decreasing the ratio of the rates of bone resorption to bone deposition in a host animal, e.g., in the treatment of osteoporosis.

10 Claims, No Drawings

ANTIOSTEOPOROTIC AGENTS

This invention relates to a process for modifying the balance between bone production and bone resorption in a host animal, including man, and more specifically to novel antiosteoporotic agents.

Osteoporosis is a common condition in adults which is evidenced by a decrease in bone density throughout the body. In fact, both the bone mineral (calcium phosphate called "hydroxyapatite") and the matrix (protein called "collagen") are slowly lost. This condition may begin to occur in humans as early as age 30. In general, the process is more rapid in women than in men. However, after age 80 there is no sex difference in the incidence of osteoporosis. In the course of 10 to 20 years of bone loss there may be symptoms of back pain and X-ray evidence of deformation of the back bone. At older ages, the brittleness of the bones becomes evident by the ease in which the hip bone fractures as the result of a simple fall. Osteoporosis is the most common cause of fractures in people over age 45.

Although the cause of osteoporosis is poorly understood, it is believed that there is an imbalance between bone production and bone resorption (bone breakdown). Bone remains a dynamic tissue throughout the life of an animal. That is, new bone is continuously being formed and old bone is continuously being resorbed. However, in animals suffering from an osteoporotic condition, bone resorption exceeds bone formation.

A survey indicates that in the United States there may be four million osteoporotic patients with serious symptoms such as vertebral fractures (D. Whedon, *Clinical Endocrinology*, II, 349–376 (1968)). Moreover, it is estimated that there are currently another 10 million persons suffering from osteoporosis who have not yet developed symptoms. Various types of osteoporosis are designated according to special conditions believed to be causative: senile (aging); post-menopausal (female loss of estrogenesis); disuse (chronic immobilization); steroid (long term steroid treatment as in arthritis). Osteoporosis may also be manifested in dental problems since the jaw bone appears to lose mass more rapidly than any other bone. Thus, periodontal disease involving a loosening of the adult teeth may be an early sign of osteoporosis.

The mechanism of bone loss is at present poorly understood. Moreover, the present methods of treatment are generally unsatisfactory. These include anabolic agents, various drugs containing phosphorous, Vitamin D, estrogens, calcium salts, fluorides and calcitonin.

Anabolic agents and estrogen therapy have been the therapy of choice for osteoporosis in post-menopausal women. Unfortunately, recent studies have indicated that patients taking estrogens may have an increased incidence of cancer of the uterus and breast. Thus, the advisability of longer-term use of such treatments would appear to be questionable.

Physical therapy is another method currently used to treat osteoporosis since immobilization can cause osteoporosis at any age. Thus, many physicians believe that exercise and physical therapy can prevent the progression of the disease in elderly patients. However, physical therapy can be harmful for patients with fractures and moreover, overstrenuous exercise can cause fractures in patients with severe osteoporosis.

Other treatments include the administration of a fluoride salt such as sodium fluoride which has been shown to promote bone growth clinically, apparently by stimulating collagen synthesis. However, a serious side effect is poorly calcified, irregular bone growth. Another treatment involves infusion of calcium and Vitamin D to counteract the deficiency of calcium or impaired absorption of calcium which is symptomatic in some elderly patients. There is, however, no evidence that a higher intake of calcium will prevent osteoporosis or increase bone mass and it could increase urinary calcium excretion.

The most promising therapeutic approach to the treatment of osteoporosis is the administration of agents which have been designed to modify the balance between the rate of bone production and the rate of bone resorption in such a manner that the ratio of the former to the latter is increased, resulting in no net bone loss. After the previously occurred bone losses have been restored, a steady state is reached where the rate of bone production and rate of bone resorption are equal. Such a modification may be effected by stimulating the physiological mechanism of bone deposition, i.e., bone formation, or by retarding the mechanism of bone resorption, or both. Drugs presently in use or in the experimental stages for accomplishing these purposes include inorganic phosphate type drugs, calcitonin and mithramycin. However, all of these drugs suffer serious drawbacks.

Mithramycin, an antibiotic, has anti-tumor activity together with hypocalcemic activity, i.e., effects a lowering of serum calcium which in turn is believed to be indicative of a decrease in the relative rate of bone resorption—i.e., bone resportion relative to bone production. Side effects, however, include nausea and renal and hepatic toxicity. Likewise, the inorganic phosphates (called "phosphonates") have side effects which include extraskeletal calcification, hypotension and renal failure, while calcitonin presents an immunological problem by virtue of its being derived from a foreign, e.g., bovine, etc., source. Thus, none of the foregoing agents are at present suitable for use in the treatment of osteoporosis.

The search for new bone resorption and/or bone deposition modifying agents has, accordingly, continued. Recently, it has been shown that 2-thiopene carboxylic acid (hereinafter referred to as 2-TCA) is a markedly effective hypocalcemic agent (see V. S. Fang et al; *Endocrinology*, 85, 763, 1969; Fang et al, *Science*, 172, 163, 1971). It was thus theorized that 2-TCA would be capable of reducing the relative rate of bone resorption and this theory has subsequently been verified. However, in certain animal tests 2-TCA has not proven to be effective in preventing bone loss. As will be hereinafter demonstrated, the present invention provides agents which are even more effective than 2-TCA in modifying the relative rate of bone resorption.

It is an object of this invention to provide a method wherein a host animal, including man, suffering from osteoporosis is treated in order to modify the balance between the rates of bone deposition and bone resorption in said host animal whereby the ratio of the latter to the former is reduced.

It is another object of this invention to provide a process for the treatment of a host animal in order to prevent the deterioration of existing healthy bone tissues in said host animal.

It is a further object of this invention to provide a process for the treatment of periodontal disease.

It is yet another object of this invention to provide a treatment for facilitating the healing of damaged bones.

These and other objects are achieved by the practice of this invention which, briefly, comprises administering to a host animal, including man, a compound of the formula:

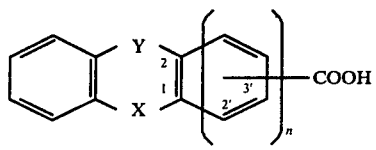

wherein Y represents $(C=O)_m$, m has a value of 0 or 1; n has a value of 0 or 1 and X represents S, NH or O, provided that there is a COOH substituent at the 1, 2 or 3 position relative to the X group; and further provided that when X is NH and n is 0, the COOH group cannot be at the 2 position; or their nontoxic, pharmaceutically acceptable salts. It is to be understood that when the value of n in the above formula is 0, the COOH group will be attached directly to the heterocyclic ring and that the benzene ring at the left of the above structure will in all cases remain unsubstituted.

Pharmaceutically acceptable salts include the nontoxic metallic salts such as sodium, potassium, calcium and aluminum, the ammonium salt and substituted ammonium salts, e.g., salts of such nontoxic amines as trialkylamines including thiethylamine, lysine, procaine, dibenzylamine, N-benzyl-beta-phenethylamine, 1-ephenamine-N,N'-dibenzylethylenediamine, N-(lower-)alkylpiperidine, e.g., N-ethylpiperidine.

These compounds are administered in any physiologically acceptable method, e.g., orally or parenterally. In physiologically acceptable quantities, e.g., from about 10 μg. to 200 mg. per kg. body weight, preferably from about 0.5 mg. to 200 mg. per kg. body weight, and most preferably from about 2 mg. to 50 mg. per kg. of body weight, they are capable of reducing the relative rate of bone resorption and are thus useful in, for example, the treatment of osteoporosis.

Methods for preparing the following compounds, corresponding to the above formula, are described in Experiments 1-4.

It will be appreciated from the following formulae that the statement "there is a COOH substituent at the 1, 2 or 3 position relative to the X group", which is used to define the compounds corresponding to the above formula, means that the COOH group is situated on either the first, second or third carbon atom adjacent the X group as indicated by the numbers "1", "2", "2'" and "3'" in the above formula.

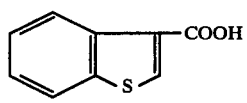
371-25

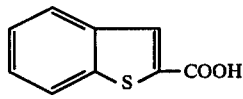
327-9

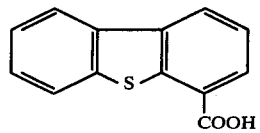
356-3

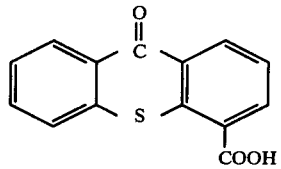
356-19

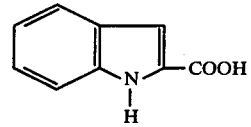
371-59

The above compounds are hereinafter referred to by the code numbers appearing below the respective formulae.

EXPERIMENT 1

Thionaphthene-2-carboxylic acid (327-9) — Thionaphthene was treated in a carboxylation reaction in accordance with the procedure described by D. A. Shirley and M. D. Cameron, in J. Am. Chem. Soc., 72, 2788, 1950 using N-butyllithium in ether, followed by carbonation with dry ice, and hydrolysis to the acid. The product had a melting point of 238° - 239° C.

Analysis: Calc'd: C, 60.66; H, 3.39; S, 17.99; Found: C, 60.75; H, 3.55; S, 18.06.

EXPERIMENT 2

Thionaphthene-3-carboxylic acid (371-25) — This compound was prepared from 3-bromothionaphthene by a Grignard reaction utilizing magnesium in ether, followed by carbonation with dry ice, and hydrolysis to the acid in accordance with the procedure described by Crook, J. Am. Chem. Soc., 1937 (1967). The product had a melting point of 178° - 179° C.

Analysis: Calc'd: C, 60.66; H, 3.39; S, 17.99; Found: C, 60.60; H, 3.35; S, 17.83.

EXPERIMENT 3

Dibenzothiophene-4-carboxylic acid (356-3) — This compound was prepared by the carboxylation of the lithium salt of dibenzothiophene in accordance with the procedure described by Gilman et al in J. Am. Chem. Soc., 61, 109, 1939 and Gilman et al in J. Am. Chem. Soc., 67, 1479, 1945. The product had a melting point of 253° - 255° C.

Analysis: Calc'd: C, 68.40; H, 3.53; Found: C, 68.07; H, 3.57.

EXPERIMENT 4

Thioxanthene-9-one-4-carboxylic acid (356-19) — This compound was prepared by adding dropwise a solution of thioxanthene in n-butylether to a solution of n-butyllithium in hexane. The intermediate product was carbonated with dry ice and acidified with hydrochloric acid. The final product had a melting point of greater than 300° C.

Analysis: Calc'd: C, 63.93; H, 3.27; S, 13.12; Found: C, 64.53; H, 3.26; S, 13.39.

Indole-2-carboxylic acid (371-59) is commercially available.

The following examples serve to illustrate the effectiveness of the antiosteoporotic agents of the present invention:

EXAMPLE 1

It has recently been shown that the bone remodeling hormones, e.g., thyrocalcitonin (TCT), is capable of reducing bone resorption rates. Accompanying this reduction, physiologically, is an increase in the production of cyclic adenosine-3',5'-monophosphate (c-AMP). Accordingly, the effectiveness of any given bone resorption modifying agent may be determined by measuring the effect of that particular agent on the production of c-AMP, utilizing isolated bone cells as the test medium according to the methods of Rodan et al, J.B.C., Vol. 429, p. 306, 1974; Rodan et al, Science, Vol. 189, p. 467, 1975. In accordance with these methods, compounds of the present invention were tested at a concentration of 2 μg. per ml. of water, at a pH of 7.4 buffered. The screening method measured accumulation of c-AMP in bone cells isolated from newborn rats' calvaria. Theophylline was used in the system as a phosphodiesterase inhibitor, since phosphodiesterase would otherwise destroy c-AMP. C-AMP was measured by radioimmunoassay. The results set forth in Table 1 are presented in the form of percent activity which was calculated by comparing the production of c-AMP produced by the compound being tested relative to the c-AMP produced by TCT. Specifically, the results were calculated according to the formula:

TABLE 1

| Compound | Percent Activity |
|----------|------------------|
| 371-25   | 200              |
| 356-3    | 150              |
| 371-59   | 100              |
| 327-9    | 80               |
| 356-19   | 56               | wherein the term "control" refers to bone cells which were treated with no compound. As can be seen from the above equation, when TCT is used as the test compound, "Percent Activity" will have a value of 100. Thus, the "Percent Activity" value for each compound is actually a comparison of the activity of the test compound with that of TCT.

$$\text{Percent Activity} = \frac{c\text{-AMP}_{test\ compound} - c\text{-AMP}_{control}}{c\text{-AMP}_{TCT} - c\text{-AMP}_{control}} \times 100$$

In summary, the foregoing data demonstrate the effectiveness of antiosteoporotic agents of the present invention in stimulating the production of c-AMP. It can be seen that the most effective compound was twice as effective as TCT in stimulating the production of c-AMP while the least effective compound was more than half as effective as TCT. In view of the correlation between stimulation of c-AMP production and bone resorption rates, it can be seen that the foregoing compounds are surprisingly effective bone resorption modifiers.

EXAMPLE 2

The procedure of Example 1 was repeated utilizing 2-TCA as the best compound. Results were calculated in the same manner as above. It was found that 2-TCA exhibited a percent activity of 30.

In comparison, compounds of the present invention, as shown in Example 1, have percent activity ranging from 200 to 56. It has thus been demonstrated that compounds useful in this invention are more effective than 2-TCA in stimulating c-AMP production.

EXAMPLE 3

The following bone tissue culture investigations were performed utilizing compounds 327-9 and 356-3 to determine the in vitro activity of these compounds. Newborn rat tibiae were incubated in culture media in accordance with the procedure described by Rodan et al in Calcified Tissue Res., Vol. 18, p. 125, 1975, with and without the drugs at a concentration of 20 mg. of drug/ml. of water at a pH of 7.4 for eight days. Among the parameters measured, only the calcium content was found to differ significantly between the treated bone tissue and the contralateral control (untreated bone tissue). The results are presented in the following table:

| Drug    | Treated Tibia (grams) | Contralateral Tibia (grams) | P*    |
|---------|-----------------------|------------------------------|-------|
| 356-3   | 12.44 ± 0.74          | 11.75 ± 0.16                 | 0.1   |
| 327-9   | 12.92 ± 0.08          | 11.71 ± 0.05                 | 0.05  |
| Control | 12.05 ± 0.08          | 11.93 ± 0.64                 | NS**  |

*Proportion (estimated on the basis of students' tests for comparison of paired values).
**Not significant.

It can be seen that bone tissue treated with the antiosteoporotic agents of this invention (356-3 and 327-9) actually had a larger calcium content than untreated bone tissues. Accordingly, it will be appreciated that treatment of bone tissues in accordance with the methods of the present invention results in a decrease of the ratio of the rates of bone resportion to bone deposition.

EXAMPLE 4

The procedure of Example 3 was repeated utilizing 2-TCA as the test compound. As can be seen from the results below, 2-TCA had no significant effect on calcium content.

| Drug  | Treated Tibia | Contralateral Tibia | P* |
|-------|---------------|---------------------|----|
| 2-TCA | 12.37 ± 0.63  | 12.15 ± 0.47        | NS |

*Proportion (estimated on the basis of students' tests for comparison of paired values).

EXAMPLE 5

The in vitro tissue culture conditions in Examples 1-4, are largely unphysiological due to the lack of vascularization, lack of mechanical stress, reduced rate of bone remodeling, lack of integration into the feedback control loops of the organism and the possible absence from the media of other necessary but unknown factors. Therefore, compound 327-9 was tested in vivo for its ability to prevent immobilization osteoporosis. Rats (150-180 g.) were utilized as the subjects in this experiment. The triceps tibial insertion (knee cap tendons) were severed in one rear leg of each rat. One group of the rats was treated for three days with 327-9 (1 mg./day by s.c. insertion) while the control group was not treated with the drug. The animals were sacrificed six days after severance of the tendons. They were then dissected and both tibiae (immobilized and non-immobilized) were removed from each animal. The tibiae were weighed and analyzed for calcium and phosphate content. The results obtained for the disuse (immobilized) tibiae were compared to the results obtained for the contralateral (non-immobilized) tibiae for each group. As seen in the following table, significant loss of weight and calcium occurred in the immobilized tibiae in the control group while this loss did not occur in the animals treated with 327-9. Moreover, the ratio of calcium to phosphate (an index of the degree of bone mineralization) was significantly higher in both tibiae bones of the animals treated with 327-9. Thus, it can be seen that the administration of 327-9 prevented the onset of osteoporotic decay of healthy bone tissue.

| | Wet Weight (gram) | | | |
|---|---|---|---|---|
| | Disuse | Contralateral | Ratio | P* |
| Control 327-9 | 0.380 ± 0.019 | 0.404 ± 0.014 | 0.94 ± 0.04 | 0.01 |
| (1 mg/d) p** | 0.394 ± 0.06 0.01 | 0.390 ± 0.050 N.S. | 1.01 ± 0.05 0.01 | N.S. |

| | Calcium Content (mmoles/bone) | | |
|---|---|---|---|
| | Disuse | Contralateral | p* |
| Control 327-9 | 0.992 ± 0.110 | 1.103 ± 0.050 | 0.01 |
| (1 mg/d) p** | 1.181 ± 0.060 0.01 | 1.121 ± 0.090 N.S. | N.S. |

| | Phosphate Content (mmoles/bone) | | |
|---|---|---|---|
| | Disuse | Contralateral | p* |
| Control 327-9 | 0.639 ± 0.050 | 0.647 ± 0.048 | N.S. |
| (1 mg/d) p** | 0.657 ± 0.060 | 0.612 ± 0.043 | 0.05 p 0.10 |

| | Calcium/Phosphate Ratio | | |
|---|---|---|---|
| | Disuse | Contralateral | p* |
| Control 327-9 | 1.050 ± 0.070 | 1.680 ± 0.160 | 0.02 |
| (1 mg/d) p** | 1.810 ± 0.210 0.01 | 1.830 ± 0.120 0.05 | N.S. |

*Proportion (estimated on the basis of students' tests for comparison of paired values.
**Estimated on the basis of students tests for comparison of population means.
N.S., not significant.

EXAMPLE 6

In this example, the dose of 327-9 was reduced to 200 μg./day. The drug was administered for six days and the rats were sacrificed nine days after the beginning of the experiment. Weight, calcium and phosphate content and the density of 110° C.-dried bones were measured. The results summarized in the following table show that at this level of treatment the drug did not prevent weight loss or a drop in the specific density of the bone. It was, however, effective in the prevention of calcium loss.

| | Dry Weight (gram/bone) | | |
|---|---|---|---|
| | Disuse | Contralateral | P* |
| Control 327-9 | 0.181 ± 0.011 | 0.187 ± 0.013 | 0.001 |
| (200 mg/d) | 1.176 ± 0.010 | 0.189 ± 0.008 | 0.001 |

| | Density (determined in mineral oil, calculated relative to water at 4° C.) | | |
|---|---|---|---|
| | Disuse | Contralateral | P* |
| Control 327-9 | 1.066 ± 0.023 | 1.119 ± 0.044 | 0.01 |
| (200 mg/d) | 1.053 ± 0.034 | 1.104 ± 0.037 | 0.01 |

| | Calcium Content (mmoles/bone) | | |
|---|---|---|---|
| | Disuse | Contralateral | P* |
| Control 327-9 | 0.926 ± 0.091 | 0.981 ± 0.059 | 0.02 |
| (200 mg/d) | 0.936 ± 0.058 | 0.936 ± 0.108 | N.S. |

| | Phosphate Content (mmoles/bone) | | |
|---|---|---|---|
| | Disuse | Contralateral | P* |
| Control 327-9 | 0.624 ± 0.089 | 0.645 ± 0.089 | N.S. |
| (299 mg/d) | 0.638 ± 0.052 | 0.632 ± 0.100 | N.S. |

*Proportion (estimated on the basis of students' tests for comparison of paired values).
N.S., not significant.

EXAMPLE 7

In this example, the effectiveness of the drugs in preventing the loss of tensile strength was measured. One leg of each animal was immobilized as described above. The drugs were injected for 10 days (s.c. 1 mg./day). The tibiae were dissected and tested for tensile strength, as determined by breaking loads. Results are presented in the following table:

| | Breaking Loads (lbs.) | |
|---|---|---|
| | Immobilized tibia | Contralateral tibia |
| Control rats | 10.0 ± 2.3 (SD) | 15.0 ± 4.1 |
| 327-9 treated | 15.9 ± 7.0 | 17.6 ± 8.9 |
| 356-3 treated | 16.9 ± 5.2 | 16.0 ± 4.9 |

It can be seen that in the control animals, immobilization caused a significant decrease in the tensile strength of the tibia whereas in the animals treated with agents of the invention, immobilization had no significant effect. Accordingly, it can be seen that the agents used in the process of the present invention were effective in preventing loss of tensile strength in the healthy bone tissue of the treated host animals.

We claim:

1. A process for the treatment of a host animal in order to modify the balance between the rate of bone resorption and the rate of bone deposition in said host animal whereby the ratio of said rate of bone resorption to said rate of bone deposition is reduced comprising administering to said host animal an amount sufficient to modify said balance and reduce said ratio, of a compound of the formula:

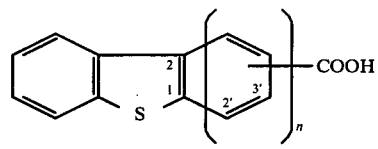

wherein n has a value of 0 or 1; provided that there is a COOH substituent at the 1, 2, 2' or 3' position relative to the S group; and further provided that when n is 0, the carboxyl group is attached to the ring containing the S group; or a nontoxic, pharmaceutically acceptable salt thereof.

2. A process in accordance with claim 1, wherein said compound is administered in an amount of from 10 m.μ. to 200 m.g. per k.g. of body weight.

3. A process in accordance with claim 1, wherein said compound is administered in an amount of from 0.5 m.g. to 200 m.g. per k.g. of body weight.

4. A process in accordance with claim 1, wherein said compound is administered in an amount of from 2 m.g. to 50 m.g. per k.g. of body weight.

5. A process in accordance with claim 1, wherein said compound has the formula:

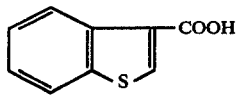

6. A process in accordance with claim 1, wherein said compound has the formula:

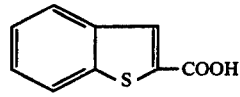

7. A process in accordance with claim 1, wherein said compound has the formula:

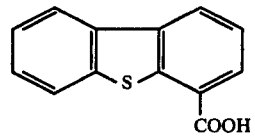

8. A process in accordance with claim 1, wherein said host animal is treated for osteoporosis.

9. A process in accordance with claim 1, wherein said host animal is being treated for periodontal disease.

10. A process in accordance with claim 1, wherein said host animal is treated to prevent the deterioration of healthy bone tissue.

* * * * *